United States Patent
Fukuchi

(10) Patent No.: US 6,514,510 B1
(45) Date of Patent: Feb. 4, 2003

(54) INSECTICIDAL AND MITICIDAL COMPOSITIONS

(75) Inventor: Toshiki Fukuchi, Yokohama (JP)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/269,542

(22) PCT Filed: Oct. 2, 1997

(86) PCT No.: PCT/JP97/03517

§ 371 (c)(1),
(2), (4) Date: Mar. 25, 1999

(87) PCT Pub. No.: WO98/14059

PCT Pub. Date: Apr. 9, 1998

(30) Foreign Application Priority Data

Oct. 2, 1996 (JP) .............................................. 8-261866

(51) Int. Cl.[7] .............................................. A01N 25/32
(52) U.S. Cl. ........................ 424/406; 424/405; 514/519; 514/520; 514/521; 514/522; 514/531; 514/427
(58) Field of Search ................................ 514/519–522, 514/531, 427; 424/405, 406

(56) References Cited

U.S. PATENT DOCUMENTS 5,965,602 A 10/1999 Takada et al. .............. 514/427
6,201,008 B1 3/2001 Takada et al. .............. 514/427

FOREIGN PATENT DOCUMENTS

EP 0 771 526 A2 5/1997

OTHER PUBLICATIONS

Chemical Abstracts, vol. 125, No. 9, 1996, 107717r.

Cotton Insect Res. Conf., p. 832 (1993) Performance of Pirate, Insecticide–Miticide, Against Cotton Pests in the Mid–South in 1992.

*Primary Examiner*—Neil S. Levy
(74) *Attorney, Agent, or Firm*—Keil & Weinkauf

(57) ABSTRACT

An insecticidal and miticidal composition comprising as active ingredients 4-bromo-2-(4-chloro-phenyl)-1-(ethoxymethyl)-5-(trifluoromethyl)pyrrole-3-carbonitrile and a pyrethroid insecticidal ingredient(s). This insecticidal and miticidal composition is effective against pests and mites which are resistant against the insecticidal and miticidal agents on the market.

4 Claims, No Drawings

INSECTICIDAL AND MITICIDAL COMPOSITIONS

The present application is a national phase entry of PCT/JP97/03517, filed Oct. 2, 1997, which claims priority of Japanese Application 261866/1996, filed Oct. 2, 1996.

TECHNICAL FIELD

This invention relates to insecticidal and miticidal compositions characterized by mixing 4-bromo-2-(4-chlorophenyl)-1-(ethoxymethyl)-5-(trifluoromethyl)-pyrrole-3-carbonitrile (hereinafter may be referred to as Compound A) and known natural pyrethroid insecticidal ingredients and/or synthetic pyrethroid insecticidal ingredients. The insecticidal and miticidal compositions of the invention can be effectively applied in the agrohorticultural field.

BACKGROUND ART

Compound A, which is an active ingredient of the insecticidal and miticidal composition of the invention, is an insecticidal and miticidal agent against agrohorticultural pests and is known to be effective against insects such as Hemiptera pests such as leaf-hoppers (Doltocephalidae), Lepidoptera pests such as diamond back moth (*Plutella xylostella*), common cutworm (*Spodoptera litura*) and apple leafminer (*Phyllonorycter ringoniella*) and Thysanoptera pests such as Thrips palmi and yellow tea thrips (*Spritothrips dorsalis*) and agrohorticultural pests such as mites such as two-spotted spider mite (*Tetranychus urticae koch*), Kanzawa spidermite (*Tetranychus kanzawai kishida*) and *Aculops pele-kassi*.

The second active ingredient of the insecticidal and miticidal composition of the invention is a pyrethroid insecticidal ingredient, of which the following compounds are representative:

As a known natural pyrethroid insecticidal ingredient, the extracted ingredient of pyrethrum, a mixture containing (Z)-(S)-2-methyl4-oxo-3-(penta-2,4-dienyl)cyclopent-2-enyl (IR)-trans-2,2-dimethyl-3-(2-methylprop-1-enyl) cyclopropanecarboxylate (Pyrethrin I) and (Z)-(S)-2-methyl-4-oxo-3-(penta-2,4-dienyl)cyclo-pent-2-enyl (E)-(IR)-trans-3-(2-methoxycarbonylprop-1-enyl)-2,2-dimethylcyclopropanecarboxylate (Pyrethrin II) and the like is mentioned.

As synthetic pyrethroid insecticidal ingredients,
2-(4-ethoxyphenyl)-2-methylpropyl 3-phenoxybenzyl ether (Ethofenprox),
(RS)-α-cyano-3-phenoxybenzyl (Z)-(1RS,3RS)-3-(2-chloro-3,3,3-trifluoropropenyl)-2,2-dimethylcyclopropanecarboxylate (Cyhalothrin),
(RS)-α-cyano4-fluoro-3-phenoxybenzyl (1RS,3RS; 1RS, 3SR)-3-(2,2-dichlorovinyl)-2,2-dimethylcyclopropanecarboxylate (Cyfluthrin),
(RS)-α-cyano-3-phenoxybenzyl (1RS,3RS,1RS,3RS)-3-(2, 2-dichlorovinyl)-2,2-dimethylcyclopro-panecarboxylate (Cypermethrin),
4-ethoxyphenyl[3-(4-fluoro-3-phenoxyphenyl)propyl] dimethylsilane (Silafluofen),
(S)-α-cyano-3-phenoxybenzyl (1R,3S)-2,2-dimethyl-3-[(RS)1,2,2,2-tetrabromoethyl]cyclopropanecarboxylate (Tralomethrin),
2-(4-bromodifluoromethoxyphenyl)-2-methylpropyl 3-phenoxybenzyl ether (Halfenprox),
2-methylbiphenyl-3-ylmethyl (Z)-(1RS,3RS)-3-(2-chloro-3, 3,3-trifluoroprop-1-enyl)-2,2-dimethylcyclopropanecarboxylate (Bifenthrin),
(RS)-α-cyano-3-phenoxybenzyl 2,2,3,3-tetramethyl-cyclopropanecarboxylate (Fenpropathrin),
(RS)-α-cyano-3-phenoxybenzyl (RS)-2-(4-chlorophenyl)-3-methylbutyrate (Fenvalerate),
(RS)-α-cyano-3-phenoxybenzyl (S)-2-(4-difluoromethoxyphenyl)-3-methylbutyrate (Flucythrinate),
(RS)-α-cyano-3-phenoxy-benzyl N-(2-chloro-α,α,α-trifluoro-p-tolyl)-D-valinate (Fluvalinate),
3-phenoxybenzyl (1RS,3RS; 1RS,3RS)-3-(2,2-dichlorovinyl)-2,2-dimethylcyclopropanecarboxylate (Permethrin) and the like are mentioned.

The above-mentioned compounds are known to be effective against agrohorticultural pests such as insects such as Hemiptera, Lepidoptera and Coleoptera insects or mites.

Hitherto, insecticidal and miticidal agents have been developed in order to control various pests such as agrohorticultural pests or hygienic pests and have been used in practice alone or in mixtures.

However, pests which have acquired resistance against various agents have been appearing as a result or the repeated use of these agents.

In particular, spider mites (Tetranychidae) have a propensity to easily develop resistance against pesticidal agents due to their ability to deposit large numbers of eggs and produce large numbers of generations which, themselves, require only a few days for development, high mutation rate and frequent inbreeding, due to minimal migration. For these reasons, two-spotted spider mite (*Tetranychus urticae koch*), Kanzawa spider mite (*Tetranychus kanzawai kishida*), *Aculops pelekassi*, and the like have acquired resistance, to some degree, against almost all existing pesticidal agents.

Therefore, in order to prevent and control the damage caused by spider mites, the development of a new insecticidal and miticidal agent which shows a high effect against spider mites which have acquired resistance against the conventional miticidal agents is highly desirable.

However, to invent an insecticidal and miticidal composition which shows no cross-resistance with existing insecticidal and miticidal agents, has no toxicity problems and has little negative impact on the environment, is extremely difficult. Moreover, a period of nearly ten years is required for a development of an invention.

Therefore, in order to apply an effective agent for an extended time, a rotational application of agents with different mechanisms of action has been adopted for good pest management practice. However, this approach does not necessarily give satisfactory results.

After a resistance problem has occurred, a countermeasure to resistance using a combination of insecticidal and miticidal agents has been studied. However, a high synergistic action has not always been found. On the other hand, Compound A, which is an active ingredient of the insecticidal and miticidal composition of the invention, was brought on the market quite recently and shows a high miticidal effect now even in a single use.

However, from the history of resistance problems of almost all miticidal agents in the past, it is likely that a similar problem might occur with Compound A, also.

The object of this invention is to provide a miticidal composition which demonstrates a high level of control against spider mites which have acquired resistance against Compound A

DISCLOSURE OF THE INVENTION

In order to provide a countermeasure to a resistance problem in spider mites against Compound A before such a problem occurs, the synergistic action with the existing insecticidal, miticidal and fungicidal agents was studied using resistant species which have been artificially established in the laboratory by selecting spider mites which have been treated with Compound A.

Thus, it has now been found that a composition which contains Compound A in combination with a pyrethroid insecticidal ingredient(s) demonstrates a joint action or synergistic effect which could not be foreseen from each individual ingredient and is very effective as an insecticidal and miticidal composition, resulting in the achievement of this invention.

Therefore, the main point of the present invention resides in insecticidal and miticidal compositions characterized by containing as active ingredients, the insecticidal and miticidal agent 4-bromo-2-(4-chlorophenyl)-1-(ethoxymethyl)-5-(trifluoromethyl)-pyrrole-3-carbonitrile (Compound A) and a pyrethroid insecticidal ingredient(s).

Representative spider mites controlled by the present invention are: two-spotted spider mite (*Tetranychus urticae koch*), *Tetranychus cinnabarinus* (Boisduval), Kanzawa spider mite (*Tetranychus Kanzawaikishida*), hawthorn spider mite (*Tetranychus viennensiszacher*), and the like.

Advantageously, the insecticidal and miticidal composition of the invention shows not only a synergistic miticidal effect against the above-mentioned spider mites, but also demonstrates simultaneous control of troublesome pests on fruit trees, for example, citrus, apple and pear, such as leaf roller moths (Tortricidae), Carposinidae, leaf miner moths (Lyonetiidae), plant bugs (Pentatomidae), aphids (Aphididae), leafhoppers (Deltociphalidae) and thrips (Thripidae); on tea plants such as leaf roller moths, aphids and thrips; on vegetables such as diamond back moths (*Plutella xylostella*), Mamestra brassicae, leaf beetles (Chrysomelidae), aphids, whiteflies (Aleyrodidae), thrips and the like.

Compound A, which is an active ingredient of the insecticidal and miticidal composition of the invention, is a known compound described in Japanese Laid-open (Kokai) Patent Publication No. 104042/89 and its method of use as agrohorticultural insecticidal and miticidal agent is also shown in the Publication. It can be synthesized according to the method described therein.

On the other hand, many compounds are known as pyrethroid insecticidal ingredients, the second active ingredient of the insecticidal and miticidal composition of the invention. Their generic names and chemical names are given below. These examples, however, of not intended to limit the scope of the invention.
Generic name: Pyrethrin I
Chemical name: (Z)-(S)-2-Methyl4-oxo-3-(penta-2,4-dienyl)cyclopent-2-enyl (IR)-trans-2,2-dimethyl-3-(2-methylprop-1-enyl)cyclopropanecarboxylate
Generic name: Pyrethrin II
Chemical name: (Z)-(S)-2-Methyl4-oxo-3-(penta-2,4-dienyl)-cyclopent-2-enyl (E)-(IR)-trans-3-(2-methyloxycarbonylprop-1-enyl)-2,2-dimethylcyclopropane-carboxylate
Generic name: Ethofenprox
Chemical name: 2-(4-Ethoxyphenyl)-2-methylpropyl 3-phenoxybenzyl ether
Generic name: Cyhalothrin
Chemical name: (RS)-α-Cyano-3-phenoxy-benzyl (Z)-(1RS,3RS)-3-(2-chloro-3,3,3-trifluoropropenyl)-2,2-dimethylcyclopropanecarboxylate
Generic name: Cyfluthrin
Chemical name: (RS)-α-Cyano4-fluoro-3-phenoxybenzyl (1RS,3RS; 1RS, 3SR)-3-(2,2-dichlorovinyl)-2,2-dimethylcyclopropanecarboxylate
Generic name: Cypermethrin
Chemical name: (RS)-α-Cyano-3-phenoxy-benzyl (1RS,3RS; 1RS,3SR)-3-(2,2-dichlorovinyl)-2,2-dimethylcyclopropane-carboxylate
Generic name: Silafluofen
Chemical name: 4-Ethoxyphenyl[3-(4-fluoro-3-phenoxyphenyl)propyl]-dimethylsilane
Generic name: Tralomethrin
Chemical name: (S)-α-Cyano-3-phen-oxybenzyl (1R,33S)-2,2-dimethyl-3-[(RS)1,2,2,2-tetrabromo-ethyl]cyclopropanecarboxylate
Generic name: Halfenprox
Chemical name: 2-(4-Bromodifluoro-methoxyphenyl)-2-methylpropyl 3-phenoxybenzyl ether
Generic name: Bifenthrin
Chemical name: 2-Methylbiphenyl-3-yl-methyl (Z)-(1RS,3RS)-3-(2-chloro-3,3,3-trifluoro-prop-1-enyl)-2,2-dimethyl-cyclopropanecarboxylate
Generic name: Fenpropathrin
Chemical name: (RS)-α-Cyano-3-phenoxybenzyl 2,2,3,3-tetramethylcyclo-propanecarboxylate
Generic name: Fenvalerate
Chemical name: (RS)-α-Cyano-3-phenoxybenzyl (RS)-2-(4-chlorophenyl)-3-methylbutyrate
Generic name: Flucythrinate
Chemical name: (RS)-α-Cyano-3-phenoxybenzyl (S)-2-(4-difluoromethoxy-phenyl)-3-methylbutyrate
Generic name: Fluvalinate
Chemical name: (RS)-α-Cyano-3-phenoxybenzyl N-(2-chloro-α,α,α-trifluoro-p-tolyl)-D-valinate
Generic name: Permethrin
Chemical name: 3-Phenoxybenzyl (1RS,3RS; 1RS,3RS)-3-(2,2-dichlorovinyl)-2,2-dimethylcyclopropane-carboxylate.

The above-mentioned names of insecticidal agents are generic names described in "Agrochemicals Handbook 1992 Edition" (Published on Jul. 30, 1992 by Japan Plant Protection Association) and "SHIBUYA INDEX-1996-(7th Edition)" (Published on Apr. 1, 1996 by ZENNOH).

In this invention, among the above-mentioned, especially the extracted ingredient of pyrethrum containing Pyrethrin I and Pyrethrin II, Ethofenprox, Cyhalothrin, Cyfluthrin, Cypermethrin, Bifenthrin, Fenpropathrin, Fluvalinate, Permethrin and the like are preferable due to a high synergistic action with 4-bromo-2-(4-chloro-phenyl)-1-(ethoxymethyl)-5-(trifluoromethyl)pyrrole-3-carbonitrile (Compound A).

The insecticidal and miticidal composition of the invention can be formulated as a wettable powder, aqueous concentrate, emulsion, liquid concentrate, sol (flowable agent), powder, aerosol, or the like, by conventional methods such as admixing Compound A and a pyrethroid insecticidal ingredient(s) with a suitable carrier and auxiliaries, such as emulsifiers, dispersants, stabilizers, suspending agents, penetrants, and the like.

The weights (%) of the insecticidal active ingredients of the composition of the invention in the above-mentioned formulations are preferably in the range of about 1–90% for wettable powders, aqueous concentrates, emulsions, liquid concentrates and sol formulations, 0.5–10% for powder formulations, and 0.01–2% for aerosol formulations.

Carriers suitable for use in the invention may be any solid or liquid carrier which is commonly used for an agrohorticultural composition and are not limited to specific substances. Various surfactants, stabilizers and other auxiliary ingredients may be used in the formulations, as necessary.

The insecticidal and miticidal composition of the invention may also be present in commercially useful formulations or application forms prepared from these formulations as a mixture with other active compounds, for example various insecticidal, miticidal, fungicidal and herbicidal agents, plant growth regulators, repellents, attractants, synergists and fertilizers and fragrances, in order to expand the applicability of the insecticidal and miticidal composition of the invention.

The mixing ratio of Compound A and the active ingredient of known pyrethroid insecticidal agent(s) are generally as follows. The ratio of the latter to 1 weight part of the former is generally 0.01–100 weight parts, and preferably is 0.5–20 weight parts.

The application method of the insecticidal and miticidal composition of the invention is as follows. Although the application amount may differ according to the numbers of pests or mites and the kinds and cultivation form of the target crop, the amount of active ingredients (total amount of Compound A and the active ingredient of known pyrethroid insecticidal agent(s)) is generally 0.1–1,000 g and preferably, 40–500 g, per 10 acres. In the case of wettable powders, aqueous concentrates, emulsions, liquid concentrates and sols, they may be diluted with water and applied to the crop at an application rate of 100–700 liters per 10 acres. In the case of powders or aerosols, the crop may be treated with the undiluted formulation.

EXAMPLES OF THE INVENTION

The insecticidal and miticidal composition of the invention is illustrated by the examples set forth hereinbelow. These examples are not intended to limit the active ingredients and their formulation ratios, auxiliary ingredients and their added amounts and the like. In the examples, parts means parts by weight.

Formulation Example 1 (Emulsion)

| | |
|---|---|
| Compound A | 10 parts |
| Fenpropathrin | 30 parts |
| Xylene | 25 parts |
| Dimethyl formamide | 20 parts |
| Sorpol 3005X polyoxyethylene type surfactant* | 15 parts |

*available from Toho Chemical Industry Ltd.

An emulsion is obtained by homogeneously mixing and dissolving the above-mentioned ingredients.

Formulation Example 2 (Wettable Powder)

| | |
|---|---|
| Compound A | 10 parts |
| Fluvalinate | 10 parts |
| Carplex #80 White carbon** | 20 parts |
| Zeeklite SP Mixture of kaolinite and cericite*** | 52 parts |
| Calcium ligninsulfonate Polyoxyethylene type surfactant**** | 8 parts |

**available from Shionogi & Co. Ltd.
***available from Zeeklite Ind.
****available from Toho Chemical Industry Ltd)

A wettable powder is obtained by homogeneously mixing the above-mentioned ingredients by jet air mill.

Formulation Example 3 (Flowable Agent)

| | |
|---|---|
| Compound A | 10 parts |
| Cypermethrin | 20 parts |
| Ethylene glycol | 8 parts |
| Sorpol AC3020***** | 5 parts |
| Xanthan gum | 0.1 parts |
| Water | 56.9 parts |

*****available from Toho Chemical Ind. Co., Ltd.)

Compound A, Cypermethrin and a previously mixed ethylene glycol, Sorpol AC3020 and xanthan gum are well mixed in water and dispersed to obtain a slurry. This slurry is then wet pulverized by Dynomill (Shinmaru Enterprises) to obtain a flowable agent.

Formulation Example 4 (POWDER)

| | |
|---|---|
| Compound A | 1 part |
| Cyhalothrin | 3 parts |
| White carbon | 5 parts |
| Clay (available from Nippon Talc Co., Ltd.) | 91 parts |

The above-mentioned ingredients are homogeneously mixed and pulverized to obtain a powder.

Formulation Example 5 (AEROSOL)

| | |
|---|---|
| Compound A | 1 part |
| Permethrin | 1 part |
| Xylene | 5 parts |
| Odorless kerosene | 93 parts |

The above-mentioned ingredients are mixed, dissolved and filled into an aerosol container and, after attaching a valve part, 60 parts of propellant (LPG/DME mixed gas) is pressed in through the valve part to obtain an aerosol.

The effectiveness and usefulness of the insecticidal and miticidal composition of the invention are demonstrated by the following test example.

Test Example 1

Test for the miticidal effect against female imagines (adults) of Kanzawa spider mite (*Tetranychus kanzawai kishida*) which are resistant to Compound A Round leaf disks (2 cm diameter) are cut out of a first leaf of kidney bean by using a leaf punch and 4 sheets of the leaf disks are placed on wet sanitary cotton on a PVC cup of 8 cm diameter. Each leaf disk is inoculated with 4 female imagines of Kanzawa spider mite (*Tetranychus kanzawai kishida*) which had acquired a strong resistance to Compound A.

After the inoculation, the insecticidal and miticidal composition of the invention, Compound A and a pyrethroid insecticidal agent(s) are dispersed in water containing 200 ppm of an extender (Sorpol 3005X, manufactured by Toho Chemical Industry Ltd.) and diluted so that a predetermined concentration of active ingredient is obtained. Each PVC cup is sprayed with 3.5 ml of the test solution by using a rotary spray tower (manufactured by Mizuho Scientific Co., Ltd.) and stored in a constant temperature chamber held at 25±° C. (32 individuals are tested per concentration, 4–5 concentrations are evaluated per formulation and 2 performances are repeated). Two days after treatment, the number of living and dead female imagines of Kanzawa spider mite (*Tetranychus kanzawai kishida*) on the leaf disk is investigated and the mortality (%) is calculated according to the formula shown hereinbelow. From these mortality data, the LC50 values are obtained by conventional probit method.

$$\text{Mortality (\%)} = \frac{\text{Number of dead mites}}{\text{Number of living mites} + \text{Number of dead mites}} \times 100$$

Further, a co-toxicity coefficient is calculated by applying Sun and Johnson's formula (J. Econ. Ent., Vol 53, p. 887, 1960) which is generally used to determine the degree of synergistic activity. The LC50 value of each individual active ingredient which constitutes the insecticidal and miticidal composition of the invention is shown in Table I. The LC50 values and the co-toxicity coefficients calculated by Sun and Johnson's formula mentioned below of the composition of the invention are shown in Table II $$\text{Co-toxicity coefficient} = \frac{\text{Actual toxicity index of mixture}}{\text{Theoretical toxicity index of mixture}} \times 100$$

For the above-mentioned values larger than 100, the larger value indicates a stronger synergistic action. For the value equal to 100, an additive action is indicated. For the values less than 100, the lesser value indicates a larger antagonistic action. A more detailed description of the calculation of the co-toxicity coefficient by the above-mentioned Sun and Johnson's method is the following. Each LC50 value of Test Compound A and Test Compound B is determined and the LC50 value of the mixture thereof M is determined.

$$\text{Actual toxicity index of mixture M} = \frac{LC_{50} \text{ of Test Compound A}}{LC_{50} \text{ of mixture M}} \times 100$$

Theoretical toxicity index of mixture M=(Toxicity index of Test Compound A×ratio of Test Compound A in mixture M (%)+ Toxicity index of Test Compound B×ratio of Test Compound B in mixture M (%))×100

Provided that the toxicity indices of Test Compound A and Test Compound B are the following:

Toxicity index of Test Compound A = 100

$$\text{Toxicity index of Test Compound B} = \frac{LC_{50} \text{ of Test Compound A}}{LC_{50} \text{ of Test Compound B}} \times 100$$

TABLE I

Effect of Compound A and pyrethroid insecticidal agents against female imago of Kanzawa spider mite which have acquired resistance against Compound A

| Test Compound | LC$_{50}$ (ppm) |
|---|---|
| Compound A | 1500 |
| Ethofenprox | 620 |
| Cyhalothrin | 590 |
| Cyfluthrin | 1500 |
| Cypermethrin | 2500 |

TABLE I-continued

Effect of Compound A and pyrethroid insecticidal agents against female imago of Kanzawa spider mite which have acquired resistance against Compound A

| Test Compound | LC$_{50}$ (ppm) |
|---|---|
| Pyrethrum | 810 |
| Bifenthrin | 20 |
| Fenpropathrin | 290 |
| Fluvalinate | 180 |
| Permethrin | 440 |

The miticidal effect of each compound is tested by using female imagines of a colony resistant to Compound A which was obtained by a long artificial selection procedure with Compound A in a laboratory on a colony of Kanzawa spider mite which had been collected in the field.

The effect of Compound A is 1500 ppm as LC$_{50}$ value. As the effect of Compound A against a susceptible strain of spider mite, which is not mentioned in the table, is about 5 ppm as LC$_{50}$ value, this strain has developed about a 300-fold resistance against Compound A.

As this Kanzawa spider mite was from a colony which had acquired resistance against pyrethroid insecticidal agents already at the time of collection in the field, all the tested pyrethroid insecticidal agents showed only low effects.

TABLE II

The effect and synergistic action of the insecticidal and miticidal composition of the invention against female imago of Kanzawa spider mite which have acquired resistance against Compound A

| Test Mixture | Mixing Ratio (Compound A: other ingredient) | LC$_{50}$ (ppm) | Co-toxicity coefficient |
|---|---|---|---|
| Compound A + Ethofenprox | 1:2 | 110 | 771 |
| Compound A + Cyhalothrin | 2:1 | 20 | 4953 |
| Compound A + Cyfluthrin | 1:1 | 34 | 4412 |
| Compound A + cypermethrin | 5:6 | 30 | 6395 |
| Compound A + Pyrethrum | 5:6 | 59 | 1736 |
| Compound A + Bifenthrin | 5:2 | 25 | 271 |
| Compound A + Fenpropathrin | 1:2 | 45 | 881 |
| Compound A + Fluvalinate | 1:4 | 57 | 383 |
| Compound A + Permethrin | 1:2 | 62 | 928 |

As the co-toxicity coefficients of the insecticidal and miticidal compositions of the invention are all values greatly exceeding 100, it is considered that a strong synergistic action between Compound A and Ethofenprox, Cyhalothrin, Cyfluthrin, Cypermethrin, Pyrethrum, Bifenthrin, Fenpropathrin, Fluvalinate or Permethrin is demonstrated in the test example.

INDUSTRIAL APPLICABILITY

The present invention provides, insecticidal and miticidal agents effective against pests and mites which are resistant against the insecticidal and miticidal agents presently on the market.

What is claimed is:

1. A method of controlling insects or mites which have acquired resistance to 4-bromo-2-(4-chlorophenyl)-1-(ethoxymethyl)-5-trifluoromethyl)pyrrole-3-carbonitrile at a locus which comprises treating the resistant insects or mites, or the locus at which the resistant insects or mites are present, with an effective amount of an insecticidal and miticidal composition comprising as active ingredients a combination of 4-bromo-2-(4-chlorophenyl)-1-(ethoxymethyl)-5-(trifluoromethyl)pyrrole-3-carbonitrile and a pyrethroid insecticidal ingredient(s) in synergistically effective amounts.

2. A method of controlling insects or mites which have acquired resistance to 4-bromo-2-(4-chlorophenyl)-1-(ethoxymethyl)-5-(trifluoromethyl)pyrrole-3-carbonitrile at a locus which comprises applying to the resistant insects or mites or the locus an effective amount of an insecticidal and miticidal composition comprising as active ingredients 4-bromo-2-(4-chlorophenyl)-1-(ethoxymethyl)-5-(trifluoromethyl)pyrrole-3-carbonitrile and a pyrethroid insecticidal ingredient(s), and wherein the insecticidal and miticidal composition comprises 0.1–5 weight parts of the pyrethroid insecticidal ingredient(s) to 1 weight part of 4-bromo-2-(4-chlorophenyl)-1-(ethoxymethyl)-5-(trifluoromethyl)pyrrole-3-carbonitrile.

3. A method of controlling insects or mites which have acquired resistance to 4-bromo-2-(4-chlorophenyl)-1-(ethoxymethyl)-5-(trifluoromethyl)pyrrole-3-carbonitrile at a locus which comprises applying to the resistant insects or mites or the locus an effective amount of an insecticidal and miticidal composition comprising as active ingredients 4-bromo-2-(4-chlorophenyl)-1-(ethoxymethyl)-5-(trifluoromethyl)pyrrole-3-carbonitrile and a pyrethroid insecticidal ingredient(s), and wherein the pyrethroid insecticidal ingredient(s) are selected from the group consisting of the following (1)–(9):

(1) extracted ingredient of pyrethrum containing (Z)-(S)-2-methyl-4-oxo-3-(penta-2,4-dienyl)cyclopent-2-enyl (IR)-trans-2,2-dimethyl-3-(2-methyl-prop-1-enyl)cyclopropane-carboxylate (Pyrethrin I) and (Z)-(S)-2-methyl-4-oxo-3-(penta-2,4-dienyl)cyclopent-2-enyl (E)-(IR)-trans-3-(2-methoxycarbonylprop-1-enyl)-2,2-dimethylcyclopropanecarboxylate (Pyrethrin II);

(2) 2-(4-ethoxyphenyl)-2-methylpropyl 3-phenoxybenzyl ether (Ethofenprox);

(3) (RS)-α-cyano-3-phenoxybenzyl (Z)-(1RS,3RS)-3-(2-chloro-3,3,3-trifluoropropenyl)-2,2-dimethylcyclopropanecarboxylate (Cyhalothrin);

(4) (RS)-α-cyano-4-fluoro-3-phenoxybenzyl (1RS,3RS;1RS,3SR)-3-(2,2-dichlorovinyl)-2,2-dimethylcyclopropanecarboxylate (Cyfluthrin);

(5) (RS)-α-cyano-3-phenoxybenzyl (1RS,3RS;1RS,3RS)-3-(2,2-dichlorovinyl)-2,2-dimethylcyclopropanecarboxylate (Cypermethrin);

(6) 2-methylbiphen-2-ylmethyl (Z)-(1RS,3RS)-3-(2-chloro-3,3,3-trifluoroprop-1-enyl)-2,2-dimethyl-cyclopropanecarboxylate (Bifenthrin);

(7) (RS)-α-cyano-3-phenoxybenzyl 2,2,3,3-tetramethylcyclopropane-carboxylate (Fenpropathrin);

(8) (RS)-α-cyano-3-phenoxybenzyl N-(2-chloro-α,α,α-trifluoro-p-tolyl)-D-valinate (Fluvalinate); and (9) 3-phenoxybenzyl (1RS,3RS;1RS,3RS)-3-(2,2-dichlorovinyl)-2,2-dimethylcyclopropanecarboxylate (Permethrin).

4. A method according to claim 2 wherein the pyrethroid insecticidal ingredient(s) are selected from the group consisting of the following (1)–(9):

(1) extracted ingredient of pyrethrum containing (Z)-(S)-2-methyl-4-oxo-3-(penta-2,4-dienyl)-cyclopent-2-enyl (IR)-trans-2,2-dimethyl-3-(2-methyl-prop-1-enyl)cyclopropane-carboxylate (Pyrethrin I) and (Z)-(S)-2-methyl-4-oxo-3-(penta-2,4-dienyl)cyclopent-2-enyl (E)-(IR)-trans-3-(2-methoxycarbonylprop-1-enyl)-2,2-dimethyl-cyclopropanecarboxylate (Pyrethrin II);

(2) 2-(4-ethoxyphenyl)-2-methylpropyl 3-phenoxybenzyl ether (Ethofenprox);

(3) (RS)-α-cyano-3-phenoxybenzyl (Z)-(1RS,3RS)-3-(2-chloro-3,3,3-trifluoropropenyl)-2,2-dimethylcyclopropanecarboxylate (Cyhalothrin);

(4) (RS)-α-cyano-4-fluoro-3-phenoxybenzyl (1RS,3RS;1RS,3SR)-3-(2,2-dichlorovinyl)-2,2-dimethylcyclopropanecarboxylate (Cyfluthrin);

(5) (RS)-α-cyano-3-phenoxybenzyl (1RS,3RS;1RS,3RS)-3-(2,2-dichlorovinyl)-2,2-dimethylcyclopropanecarboxylate (Cypermethrin);

(6) 2-methylbiphen-2-ylmethyl (Z)-(1RS,3RS)-3-(2-chloro-3,3,3-trifluoroprop-1-enyl)-2,2-dimethylcyclopropanecarboxylate (Bifenthrin);

(7) (RS)-α-cyano-3-phenoxybenzyl 2,2,3,3-tetramethylcyclopropane-carboxylate (Fenpropathrin);

(8) (RS)-α-cyano-3-phenoxybenzyl N-(2-chloro-α,α,α-trifluoro-p-tolyl)-D-valinate (Fluvalinate); and (9) 3-phenoxybenzyl (1RS,3RS;1RS,3RS)-3-(2,2-dichlorovinyl)-2,2-dimethylcyclopropanecarboxylate (Permethrin).

* * * * *